US011826257B2

(12) United States Patent
Barnett et al.

(10) Patent No.: US 11,826,257 B2
(45) Date of Patent: Nov. 28, 2023

(54) TIBIAL PREPARATION

(71) Applicant: DEPUY IRELAND UNLIMITED COMPANY, County Cork (IE)

(72) Inventors: James Barnett, Leeds (GB); Andrew Dixon, Leeds (GB)

(73) Assignee: DEPUY IRELAND UNLIMITED COMPANY, County Cork (IE)

( * ) Notice: Subject to any disclaimer, the term of this patent is extended or adjusted under 35 U.S.C. 154(b) by 334 days.

(21) Appl. No.: 17/117,197

(22) Filed: Dec. 10, 2020

(65) Prior Publication Data

US 2021/0177612 A1   Jun. 17, 2021

(51) Int. Cl.
    *A61F 2/38*    (2006.01)
    *A61F 2/46*    (2006.01)
    *A61B 17/92*    (2006.01)

(52) U.S. Cl.
    CPC ............ *A61F 2/3868* (2013.01); *A61B 17/92* (2013.01); *A61F 2/4684* (2013.01); *A61F 2002/3895* (2013.01); *A61F 2002/4687* (2013.01)

(58) Field of Classification Search
CPC .................. A61F 2/3868; A61F 2/4684; A61F 2002/3895; A61F 2002/4687; A61B 17/92
See application file for complete search history.

(56) References Cited

U.S. PATENT DOCUMENTS

| | | | |
|---|---|---|---|
| 2008/0015606 A1* | 1/2008 | D'Alessio | A61F 2/4684 606/87 |
| 2008/0119938 A1 | 5/2008 | Oh | |
| 2008/0183291 A1* | 7/2008 | Scheller | A61F 2/3872 623/908 |
| 2008/0243263 A1* | 10/2008 | Lee | A61F 2/3868 623/20.29 |

(Continued)

FOREIGN PATENT DOCUMENTS

| | | |
|---|---|---|
| EP | 0780092 A1 | 6/1997 |
| EP | 2540255 A1 | 4/2015 |

(Continued)

OTHER PUBLICATIONS

Persona Partial Knee System, Surgical Technique, 1222.3-GLBL-en-REV0817, Zimmer Biomet, 2017, 48 Pages.

(Continued)

*Primary Examiner* — Kevin T Truong
*Assistant Examiner* — Diana Jones

(57) ABSTRACT

A kit of parts for use in a unicondylar knee replacement procedure having a keel punch, a unicondylar tibial trial and an impactor. The keel punch including a cutting formation on the inferior side configured to form a slot in a resected part of a patient's tibia, and a first attachment formation on the superior side. The unicondylar tibial trial having a body defining a slot passing therethrough between an upper surface and a lower surface that extends parallel to a longitudinal axis extending from an anterior end to a pos- (Continued)

terior end of the body. The slot configured to slidably receive the keel punch. The impactor includes a second attachment formation and is releasably attachable to the keel punch by slidingly engaging the second attachment formation with the first attachment formation. An assembly for use in and methods of trialing during a unicondylar knee replacement procedure are also disclosed.

20 Claims, 6 Drawing Sheets

(56) References Cited

U.S. PATENT DOCUMENTS

| | | | | |
|---|---|---|---|---|
| 2011/0125202 | A1* | 5/2011 | Ries | A61F 2/461 606/86 R |
| 2013/0325136 | A1* | 12/2013 | Thomas | A61B 17/1735 623/20.32 |
| 2014/0276857 | A1* | 9/2014 | Major | A61F 2/3868 606/88 |
| 2014/0277548 | A1* | 9/2014 | Cohen | A61F 2/389 623/20.34 |
| 2018/0103967 | A1* | 4/2018 | Rouyer | A61B 17/1659 |

FOREIGN PATENT DOCUMENTS

| | | |
|---|---|---|
| EP | 2939615 A1 | 11/2015 |
| EP | 3395269 A2 | 10/2018 |
| WO | 2018062279 A1 | 4/2018 |

OTHER PUBLICATIONS

Sigma High Performance Partial Knee, Unicondylar Surgical Technique, 140082-200512 DSUS/EMEA, DSUS/JRC/1114/0582 Rev. 3, 2017, 2019 and 2020, 28 Pages.

Search Report From Corresponding GB Application No. GB1918534.7, dated Jun. 11, 2020, 5 Pages.

\* cited by examiner

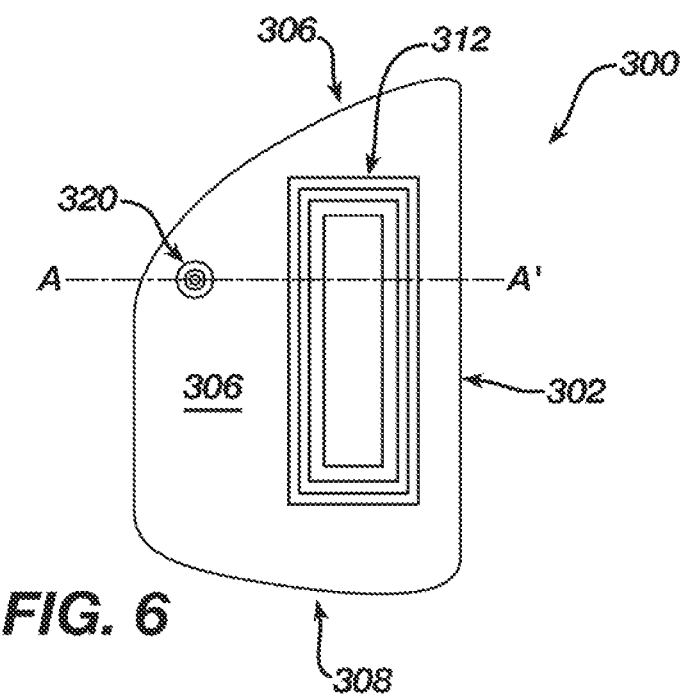
FIG. 6
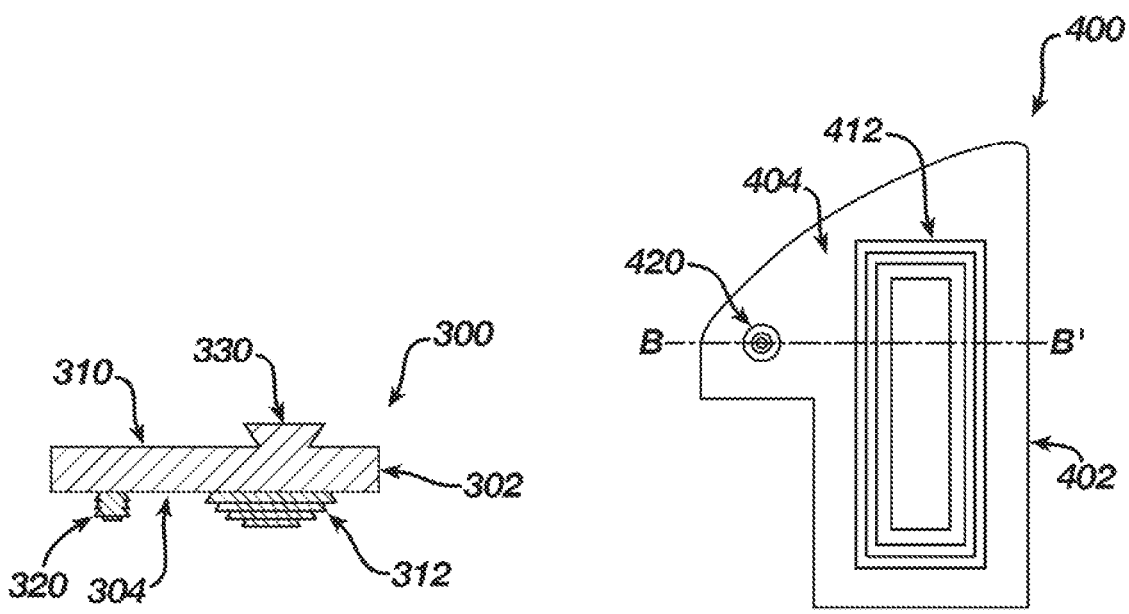
FIG. 7
FIG. 8

TIBIAL PREPARATION

CROSS REFERENCE TO RELATED APPLICATIONS

This application claims priority to GB 1918534.7 filed on Dec. 16, 2019, which is expressly incorporated herein by reference.

The present disclosure relates to surgical apparatus and methods and in particular to surgical apparatus and surgical methods relating to preparation of the tibia during a unicondylar knee arthroplasty procedure.

Knee arthroplasty procedures generally fall into two categories. Total knee replacement procedures, in which both condyles of the femur are replaced and the entire superior part of the tibia are replaced, and unicondylar or unicompartmental or partial knee replacement procedures, in which only a one of the medial and lateral condyles of the femur is replaced and a corresponding medial or lateral part of the superior part of the tibia.

For example, EP-2540255 describes an orthopaedic surgical instrument assembly for use in total knee replacement including a base trial which is positioned on a resected proximal tibia and a guide tower which may be mounted on the base trial, and aligned with an opening in the base trial, to allow a keel punch to be driven into the tibia while being guided by the guide tower.

Various surgical different surgical procedures may be used to carry out a partial knee arthroplasty often depending on the implant system being used. Generally it is preferable to try and retain, or minimally modify, the soft tissue structures of the patient's knee where possible. Also, as only a medial or lateral part of the tibia and femur are resected, the surgical space available for instrumentation and implants is quite small. It can therefore be challenging to provide instrumentation easily and reliably useable by the surgeon within such small spaces.

Typically, but not necessarily always, knee arthroplasty procedures involve a trialling step in which trial implants are used to help assess the appropriate size and/or position of the final prosthetic implant that will eventually be implanted in the patient.

For example, the Persona Partial Knee System surgical technique of Zimmer Biomet (PERSONA is a Trademark which is registered in some countries) describes a tibial trial having a recess on an upper surface, a keel on a lower surface, a fixation screw hole, a first drill guide toward the front, a second drill guide toward the side and a handle connector toward the front. In use a handle is connected to the trial and the tibial trial is positioned in the anterior-posterior direction and the handle is used to drive the keel into the resected tibial surface. If necessary, a tibial impactor may be inserted into the recess and used to impact the tibial trial until it is flush. A headed screw is used to secure the tibial trial to the tibia via the fixation screw hole and then a drill is used to drill two peg holes for receiving pegs using the two drill guides which are inclined by about 20 degrees to avoid the patient's femur.

The SIGMA High Performance Partial Knee Surgical Technique of DePuy Synthes (SIGMA is a trade mark which is registered in some countries) describes a two stage process in which a tibial template with a slot therein is positioned on the resected part of the tibial plateau and then an osteotome is used to remove bone via the slot to form a keel slot in the bone. A tibial keel trial may then be inserted through the slot into the cavity to check that adequate bone has been removed. The tibial template is then removed priori to cementation of the prepared bone surface and then use of a tibial trial to introduce and insert the tibial prosthesis.

Hence, the instrumentation required to carry out a partial knee procedure can be quite extensive and complicated.

It would therefore be beneficial to be able to provide surgical apparatus and methods which can more easily be used during a partial knee arthroplasty procedure and/or which can simplify the instrumentation needed to carry a partial knee arthroplasty procedure.

According to a first aspect of the disclosure there is provided a kit of parts for use in a unicondylar knee replacement procedure, the kit of parts comprising: a keel punch having an inferior side and a superior side, the keel punch including a cutting formation on the inferior side and configured to form a slot in a resected part of a tibia of a patient in use and a first attachment formation on the superior side; a unicondylar tibial trial comprising a body having an upper surface, a lower surface, an anterior end and a posterior end, the body defining a slot passing through the body and between the upper surface and the lower surface and wherein the slot extends parallel to a longitudinal axis of the body extending from the anterior end to the posterior end and wherein the slot is configured to slidably receive the keel punch in use; and an impactor, wherein the impactor includes a second attachment formation and the impactor is releasably attachable to the keel punch by slidingly engaging the second attachment formation of the impactor with the first attachment formation of the keel punch.

The body may further comprise a handle attachment formation adjacent the anterior end of the body for releasably receiving a handle.

The body may define a plane. An anterior part of the anterior end of the body may define a first aperture for receiving a pin, such as a bone pin or similar fixing, and wherein the first aperture extends along a first axis that is inclined relative to the plane of the body.

The anterior part of the anterior end of the body may also define a second aperture for receiving a pin, such as a bone pin or similar fixing, and wherein the second aperture extends along a second axis that is inclined relative to the plane of the body.

The first axis may be configured to permit the fixing to engage a tibia of a patient when the unicondylar tibial trial is seated in a first state on a medial resected part of the tibia. The second axis may be configured to permit the fixing to engage a tibia of a patient when the unicondylar tibial trial is seated in a second state on a lateral resected part of the tibia. The unicondylar tibial trial may be inverted in the second state compared to the first state.

The unicondylar tibial trial may further comprise a spike on an anterior part of the unicondylar tibial trial. The spike may extend in a posterior direction and/or be arranged to engage an anterior portion of a tibia of a patient in use to secure the unicondylar tibial trial to the tibia of the patient.

The body may further define a drill guide or cutting guide passing through the body between the upper surface and the lower surface. The drill guide or cutting guide may be arranged to receive a drill or cutting tool to allow a peg hole to be drilled or cut in a resected portion of a tibia of a patient.

The drill guide or cutting guide may define a drill guide axis or cutting guide axis and wherein the drill guide axis or cutting guide axis may be perpendicular to a plane defined by the lower surface of the body.

The unicondylar tibial trial may be mirror symmetric about a plane parallel to the upper surface and/or lower surface so that the unicondylar tibial trial can be inverted to be used on either a medial or a lateral resected part of a tibia.

The kit of parts may further comprise a further keel punch including a further cutting formation configured to form a slot in resected part of a tibia of a patient in use. The further keel punch may be configured to be slidably received within the slot of the unicondylar tibial trial. The cutting formation and the further cutting formation may be different.

The cutting formation may have a different length and/or a different depth and/or a different width and/or a different shape and/or a different size compared to the further cutting formation.

The kit of parts may further comprise a further unicondylar tibial trial similar to the first unicondylar tibial trial. The further unicondylar tibial trial may have a different size compared to the first unicondylar tibial trial.

The first attachment formation may be one of a male formation and a female formation and the second attachment formation may be the other of the male formation and the female formation. The male formation may be slidingly receivable within the female formation. The male formation may have the form of a dovetail and the female formation may have the form of a dovetail groove.

The impactor may comprise: a first member bearing the further attachment formation; a second member providing an impaction surface; and an intermediate member extending between the first member and second member and spacing the second member apart from and/or above the first member.

The impaction surface may define a first plane, the first member may define a second plane and the first plane and the second plane may be parallel.

The first member may be as long as, or may be longer than, the length of the keel punch.

The impactor may generally have the form of a C-arm.

The kit of parts may further comprise a trial bearing. The trial bearing may include a bearing attachment formation, and the trial bearing may be releasably attachable to the keel punch by mating the bearing attachment formation with the first attachment formation.

A second aspect of the disclosure provides an assembly of the kit of parts, wherein the impactor is attached to the keel punch by the second attachment formation mating with the first attachment formation and wherein the keel punch is located within the slot of the body.

A third aspect of the disclosure provides a unicondylar tibial trial for use in a unicondylar knee replacement procedure, comprising: a body having an upper surface and a lower surface; an attachment formation extending from the upper surface; a keel punch extending from the lower surface and configured to form a slot in a tibia of a patient in use; and a hole punch extending from the lower surface and configured to form a hole in the tibia of the patient in use.

The body may have an anterior end and may further comprise an anterior lip extending from the anterior end of the body and arranged in use to abut against an anterior surface of the tibia of the patient to limit movement of the unicondylar tibial trial along an anterior-posterior axis of the tibia of the patient.

The attachment formation may be configured for sliding engagement with a further attachment formation of an impactor.

The body may have an anterior end and a posterior end and a longitudinal axis extending between the anterior end and the posterior end and the attachment formation may extend parallel to the longitudinal axis.

The body may have an anterior end and a posterior end and a longitudinal axis extending between the anterior end and the posterior end and the keel punch may extend parallel to the longitudinal axis.

A fourth aspect of the disclosure provides a kit of parts comprising: the unicondylar tibial trial of the third aspect; and a tibial trial impactor having a further attachment formation configured to releasably connect to the attachment formation.

The tibial trial impactor may comprise: a first member bearing the further attachment formation; a second member providing an impaction surface; and an intermediate member extending between the first member and second member and spacing the second member apart from and/or above the first member.

The lower surface of the body may define a first plane, the impaction surface may define a second plane and the tibial trial impactor may be configured to position impaction surface with the second plane parallel to the first plane when the tibial trial impactor is connected to the unicondylar tibial trial.

The first member may be as long as, or may be longer than, the keel punch.

The tibial trial impactor may generally have the form of a C-arm.

A fifth aspect of the disclosure provides an assembly of the kit of parts of the fourth aspect wherein the tibial trial impactor may be attached to the unicondylar tibial trial by the further attachment formation mating with the attachment formation.

A sixth aspect of the disclosure provides a method of trialling during a unicondylar knee replacement procedure being carried out on a patient, comprising: positioning a unicondylar tibial trial having a slot passing through the unicondylar tibial trial on a resected portion of a tibia of the patient with the lost parallel to the anterior-posterior axis of the tibia; introducing a keel punch attached to an impactor into the slot in the unicondylar tibial trial; and impacting the impactor to form a slot in the resected portion of the tibia and parallel to the anterior-posterior axis of the tibia using the keel punch.

The method may further comprise removing the impactor and leaving the keel punch in place in the unicondylar tibial trial.

The method may further comprise: introducing a cutting instrument into a guide hole passing through the unicondylar tibial trial and forming a hole in the resected portion of the tibia.

The method may further comprise attaching a trial bearing to the keel punch in the unicondylar tibial trial.

The tibial trial impactor may be attached to the unicondylar tibial trial using an attachment formation on an upper surface of the unicondylar tibial trial. The trial bearing may be attached to the unicondylar tibial trial using the attachment formation.

An seventh aspect of the disclosure provides a method of trialling during a unicondylar knee replacement procedure being carried out on a patient, comprising: attaching a tibial trial impactor to a unicondylar tibial trial having a keel punch and a hole punch extending from a lower surface of the unicondylar tibial trial; using the tibial trial impactor to introduce the unicondylar tibial trial into a joint space between a femur of the patient and a resected portion of a tibia of the patient and to position the unicondylar tibial trial over the resected position of the tibia; and impacting the tibial trial impactor to form a hole using the hole punch and a slot using the keel punch in the resected portion of the tibia at the same time.

The method may further comprise: removing the tibial trial impactor from the unicondylar tibial trial; and attaching a trial bearing to the unicondylar tibial trial, wherein the tibial trial impactor is attached to the unicondylar tibial trial using an attachment formation on an upper surface of the unicondylar tibial trial and wherein the trial bearing is attached to the unicondylar tibial trial using the attachment formation.

According to an eighth aspect of the disclosure, there is provided an orthopaedic system for a unicondylar knee replacement. The system comprises a keel punch having an inferior side and a superior side. The keel punch includes a cutting formation on the inferior side and configured to form a slot in a resected part of a tibia of a patient in use and a first attachment formation on the superior side. The system may also comprise a unicondylar tibial trial comprising a body having an upper surface, a lower surface, an anterior end and a posterior end. The body defines a slot passing through the body and between the upper surface and the lower surface. The slot extends parallel to a longitudinal axis of the body extending from the anterior end to the posterior end. The slot is configured to slidably receive the keel punch in use. The system may also comprise an impactor that includes a second attachment formation, and the impactor is releasably attachable to the keel punch by slidingly engaging the second attachment formation of the impactor with the first attachment formation of the keel punch.

The system may further comprise a further keel punch including a further cutting formation configured to form a slot in resected part of a tibia of a patient in use. The further keel punch may be configured to be slidably received within the slot of the unicondylar tibial trial. The cutting formation and the further cutting formation may be different.

The orthopaedic system may further comprise a further unicondylar tibial trial similar to the first unicondylar tibial trial. The further unicondylar tibial trial may have a different size compared to the first unicondylar tibial trial.

The orthopaedic system may further comprise a trial bearing. The trial bearing may include a bearing attachment formation, and the trial bearing may be releasably attachable to the keel punch by mating the bearing attachment formation with the first attachment formation.

Embodiments will now be described in detail, by way of examples only, and with reference to the accompanying drawings, in which:

FIG. 6 shows an elevation from below of an instrument according to a further aspect of the disclosure of a further kit of parts;

FIG. 7 shows a transverse cross section through the instrument shown in FIG. 6;

FIG. 8 shows an elevation from below of a further instrument similar to that shown in FIG. 6.

Figure 1:
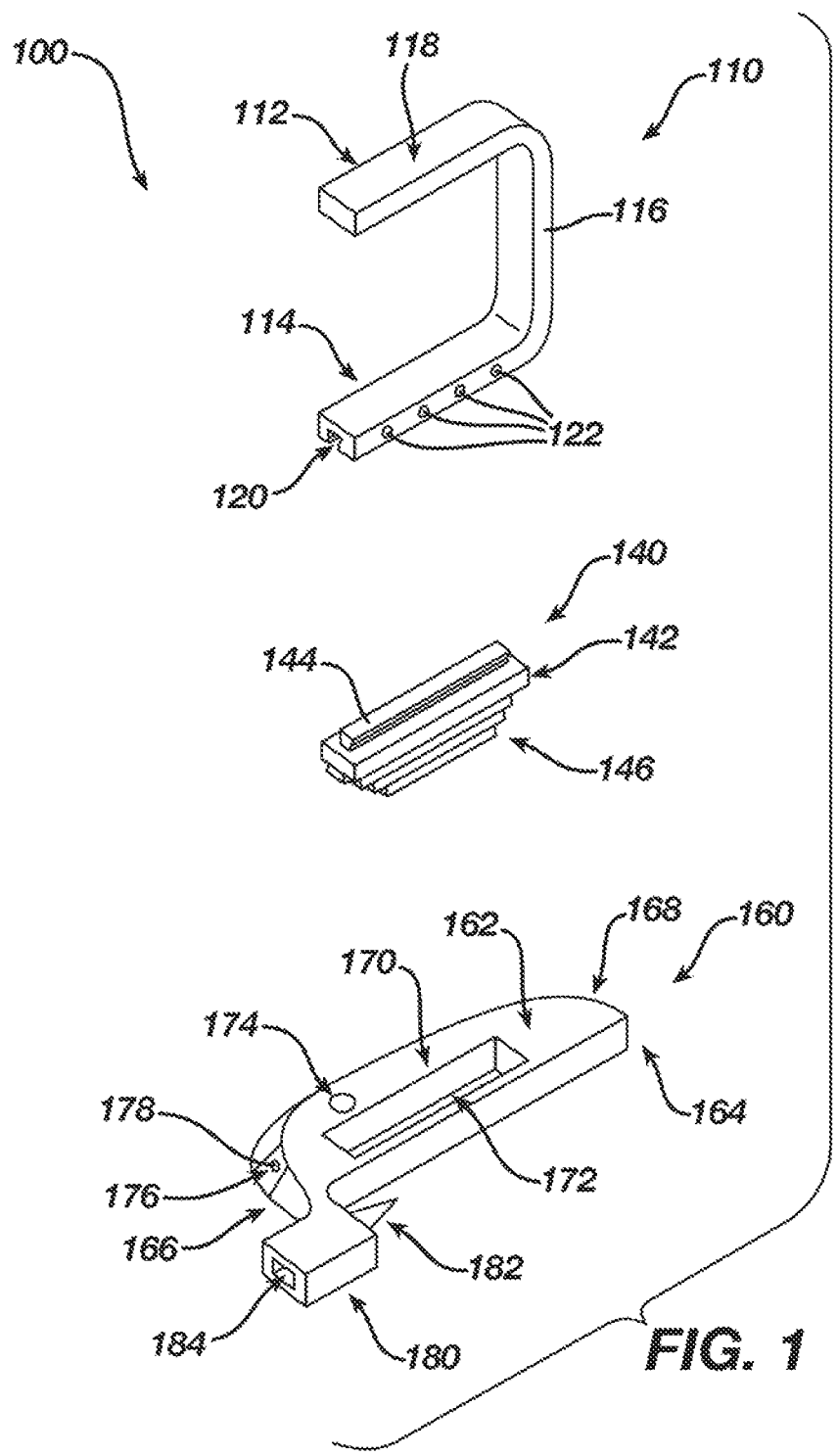
FIG. 1 shows a perspective view of a kit of parts according to an aspect of the disclosure and including various instruments according to various aspects of the disclosure for use in a unicondylar knee replacement procedure.

Like items in the different Figures of drawings share common reference numeral unless indicated otherwise.

With reference to FIG. 1, there is shown a perspective view of some of the instruments of a kit of parts for use in a unicondylar knee replacement surgical procedure 100. The kit of parts 100 includes an impactor 110, a punch or broach 140 and a unicondylar tibial trial 160.

The impactor 110 includes a first member 112, a second member 114 and an intermediate member 116 connecting the first and second members and holding the first member generally above and in registration with the second member 114. As illustrated in FIG. 1, the impactor has a generally c-arm form. An upper surface 118 of the second member 112 provides an impaction plate via which an impaction force can be applied using the impactor 110.

The second member 114 defines a dovetail shaped cavity 120 extending along a longitudinal axis of the second member 112 and in a lowermost surface of the second member 114. Dovetail cavity 120 provides an attachment formation via which the impactor 110 may be releasably attached to the punch 140 as described in greater detail below.

A plurality of spring-ball assemblies or live spring recesses are provided in respective recesses on either side of the channel 120 to increase the strength of the connection between the impactor 110 and punch 140.

The length of the intermediate member 116 is sufficient such that the condyles of a femur may be received in the gap between the first and second members in use.

The punch or broach 140 has a generally rectangular body 142 extending along a longitudinal axis. A dovetail shaped male formation 144 extends along the longitudinal axis of the body 142 and is dimensioned to be snugly received within the dovetail cavity 120 of the impactor 110. A plurality of cutting formations 146 extend from a lower surface of the body 142. The cutting formations 146 are configured to form a slot within the bone of a tibia of a patient in use. In the illustrated embodiment, the plurality of cutting formations generally have the form of a stepped pyramid with a plurality of sharp edges. However, in other embodiments, other cutting formations may be used instead.

Figure 2:
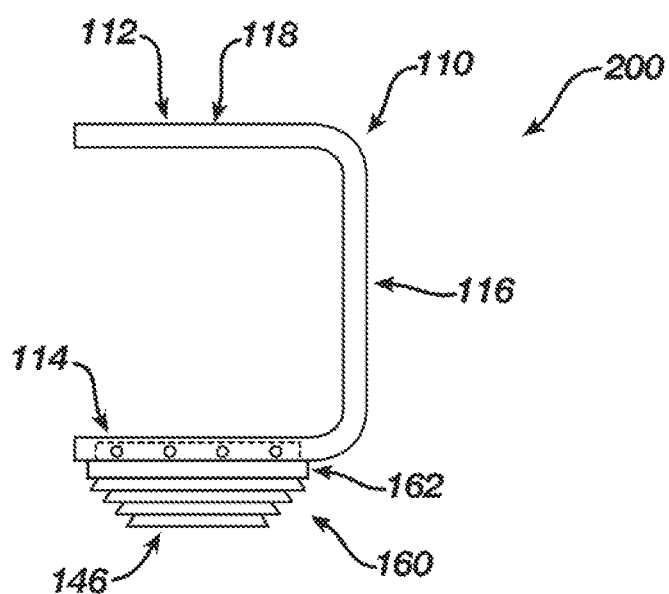
FIG. 2 shows a side elevation of an assembly of two of the parts of the kit of parts illustrated in FIG. 1.

FIG. 2 shows a side elevation of an assembly 200 of the impactor 110 and the punch 140. The assembly 200 may be formed by sliding the male dovetail formation 144 into and along the dovetail cavity 120 of the impactor 110. As illustrated, the second member 114 has a length slightly greater than the length of the body 142 of the punch 140. Also, the first member 112 has a length generally the same as the length of the second member 114. Also, the impaction surface 118 lies in a plane generally parallel to the plane defined by the body 142 of the punch 140. This arrangement allows a significant impaction force to be transferred to the punch 140 by striking the impaction surface 118 in use.

Returning to FIG. 1, the kit of parts also includes a unicondylar tibial trial 160. In particular, the unicondylar tibial trial 160 can be considered a base component of a unicondylar tibial trial as, in use, a bearing trial component is also used for the full unicondylar tibial trial. For the sake of brevity, the unicondylar tibial trial 160 will generally be referred to as simply the tibial trial, although it will be understood that it is for a partial, unicompartmental or unicondylar knee replacement surgical procedure.

The tibial trial 160 has a generally plate like construction and includes an upper surface 162 and a lower surface 164. The trial has a profile matching the corresponding final implant. The trial 160 also has an anterior end 166 and a posterior end 168. A longitudinal axis or anterior-posterior axis of the trial extends from the anterior end to the posterior end.

The main body 170 of the tibial trial 160 defines a generally rectangular slot passing through the body from the upper surface to the lower surface. The slot 172 extends generally along, or parallel to, the anterior-posterior axis of the tibial trial 160. The slot 170 is dimensioned to slidingly receive the body 142 of the punch 140 in use as described in greater detail below.

The tibial trial 160 also includes a drill guide 174 in the form of a generally circular cylindrical hole passing through the body 170 from the upper surface to the lower surface. As illustrated in FIG. 1, the drill guide 174 is positioned to the side of the slot 172 and which may be either in a medial or lateral direction relative to the patient's anatomy depending on the leg of the patient and the orientation in which the tibial trial 160 is being used.

An anterior part 176 of the tibial trial 160 defines a first fixation hole 178 which has an axis extending in a generally tilted direction relative to the plane of the body 170 of the tibial trial 160. The fixation hole, in use, can receive a fixing, for example, a bone pin to secure the tibial trial 160 to the resected tibia of the patient in use. Although not visible in FIG. 1, a second fixation hole is also provided on an underside of the tibial trial 160 and similarly inclined relative to the plane of the body of the tibial trial. The second fixation hole may receive a fixing, such as a bone pin, in use, to secure the tibial trial 160 to a resected tibia of a patient when then tibial trial 160 is turned upside down or inverted. Hence, the same tibial trial 160 is generally symmetric about the plane defined by its main body 170 such that the same tibial trial 160 can be used in a first orientation (illustrated in FIG. 1) and a second inverted orientation in which it is turned upside down, so as to be able to use on medial and lateral L-cuts of a patient's tibia.

As also illustrated in FIG. 1, a further anterior portion 180 of the tibial trial 160 is provided. A spike or other sharp male formation 182 extends therefrom in a generally posterior direction and may engage with the tibial eminence or other central anatomical feature of the tibia to at least partially secure the tibial trial 160 to the resected tibia in use. Also, a handle attachment formation 184 is provided to which a handle may be releasably attached to a handling and insertion of the tibial trial 160 into the bone gap in use.

Figure 3:
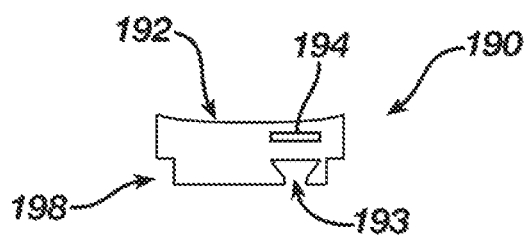
FIG. 3 shows an end elevation of a further part of the kit of parts and being a trial bearing.

With reference to FIG. 3, there is shown a front elevation of a bearing trial component 190 which is used with the base tibial trial component 160 to form the entire tibial trial. The bearing component 190 has a curved articulating surface 192 matching the implant. A connection feature 194 may also be provided toward an anterior end of the bearing component 190 to receive a handle or other handling instrument. A dovetail shaped channel 196 is defined in a lower surface of a body 198 of the bearing component 190. Dovetail chanel 196 extends generally along an anterior-posterior axis of the bearing component 190 and is shaped and dimensioned to slidingly engage with the male dovetail formation 144 on the punch 140 as illustrated in FIG. 1. Hence, dovetail groove 196 provides a releasable attachment formation by which the bearing trial component 190 may be releasably attached to the punch 140 in use, as described in greater detail below.

The bearing trial component 190 is a further part of the kit of parts 100 illustrated in FIG. 1. Generally, the kit of parts 100 may include one instance of the impactor 110. A plurality of different sized punches 140 may be provided. Generally, the different punches will all have the same sized body part 142 and attachment formation 144 but will have different sized cutting formations 146. For example, the length, width or depth of the cutting formations 146 may be varied in order to form a different sized slot within the resected tibial surface. The required size of the slot will depend on the size of the intended prosthetic implant as the size of the keel element of the prosthetic implant may vary with prosthetic implant size.

Similarly, the kit of parts 100 may include a plurality of different sized tibial trial components 160. The length and width and depth of the tibial trial component 160 may be varied to correspond to different sized prosthetic tibial components. The dimensions of the slot 172 may be similar between different sized tibial trial components. In other embodiments, if the size of the slot varies with the size of the tibial trial component 160, then the size of the body 142 of the keel punch 140 may also vary accordingly.

Similarly, the kit of parts may include different size bearing trial components 190 each corresponding to different sized prosthetic tibial components.

A method of using the instruments of the kit of parts 100 in a unicondylar knee replacement surgical procedure will not be described with reference to FIG. 4.

Figure 4:
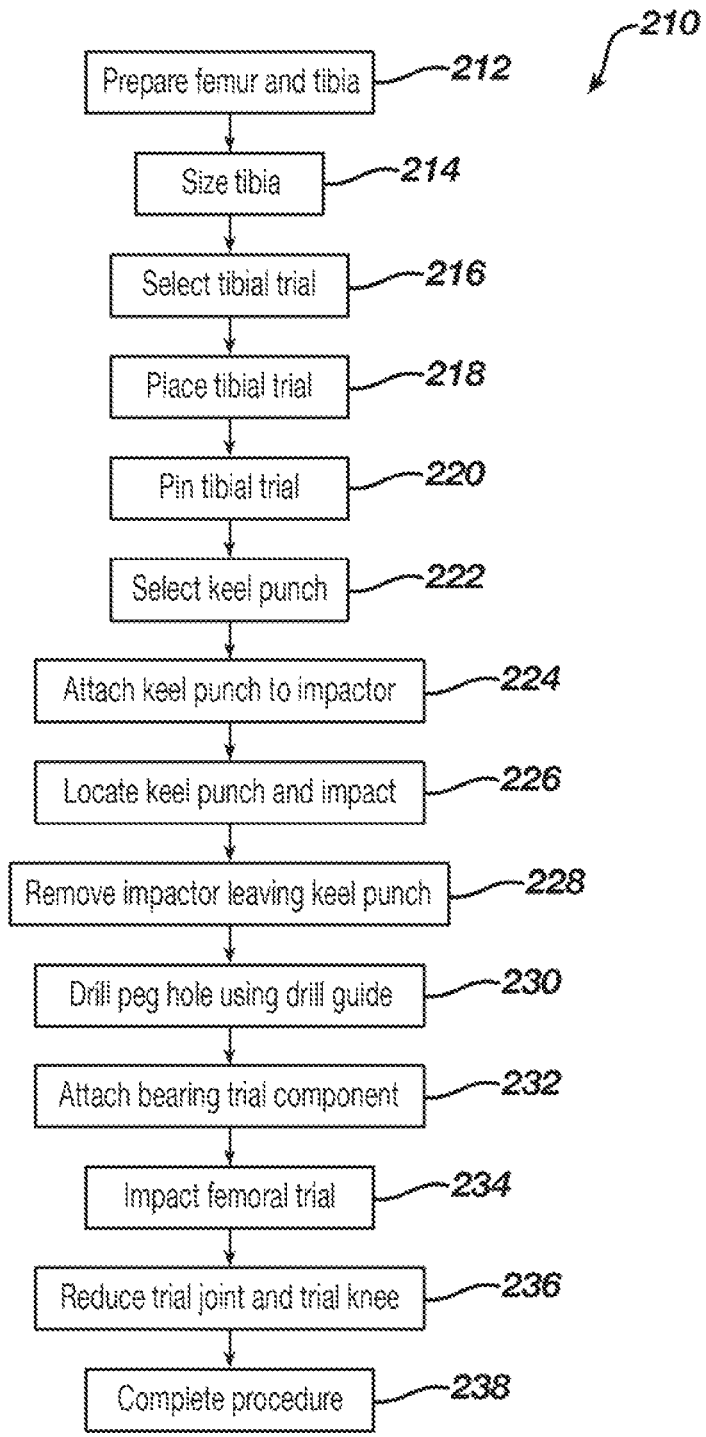
FIG. 4 shows a flow chart illustrating a method according to an aspect of the disclosure of using the kit of parts illustrated in FIGS. 1 to 3.

FIG. 4 shows a flow chart illustrating a unicondylar knee replacement surgical procedure 210 and in particular various trialling steps using the instrumentation described above. Many of the steps preceding and following the trialling activities may be generally conventional, and are therefore not described in detail. Initially, various conventional surgical steps may be carried out to prepare the femur and tibia at 212 including making various cuts to the distal portion of the femur and proximal portion of the tibia. As this is a unicondylar procedure, only a medial or lateral part of the tibia is resected. Generally, an L-cut is made to resect the tibia thereby removing the proximal medial or lateral portion thereof. As described earlier, the tibial trial 160 is generally symmetrical and therefore can be used on either the medial or lateral side of a tibia simply by inverting it.

At 214, a sizing instrument may be used to determine the size of the tibia in terms of its length in the anterior-posterior direction and width in the medial-lateral direction. Using the sizing information obtained at step 214, a one of the pluralities of tibial trials provided in the kit of surgical instrumentation may be selected having a size most closely matching that determined at step 214. Having selected an appropriately sized tibial trial, a handle may be attached via handle connection 184 and used to place the tibial trial 160 on the resected portion of the tibia at step 218. In particular, the handle may be used to force spike 182 into an interior portion of the tibia in order to initially secure the tibial trial 160 to the resected tibia.

At 220, a fixing, such as a bone pin, is inserted via fixing hole 176 so as to pin the tibial trial to the tibia and further stabilise the tibial trial. As explained above, the fixing hole 176 is inclined relative to the plane of the tibial trial and therefore allows the bone pin to be directed toward and driven into an anterior portion of the tibia.

As also explained above, a plurality of different sized keel punches 140 are provided in the kit of surgical instrumentation. Hence, at 222, an appropriately sized keel punch is selected from the plurality of keel punches. The size of the keel punch may be determined both by the size of the tibial trial 160, and also the size of the keel of the intended prosthetic tibial implant. Once a suitably sized keel punch has been selected at 222, then the keel punch is attached to the impactor 110 at step 224 by engaging male dovetail formation 444 with dovetail channel 120 and sliding the keel punch on to the impactor 110. During this part of the procedure, the patient's knee is in flexion. The impactor 110 may then be used to introduce the keel punch 140 into the slot 172 of the tibial trial 160 and the resected femur is received within the concavity defined by the c-arm shape of the impactor 110. Once the keel punch 140 has been located in slot 172, an impaction tool, such as a mallet, may be used to strike impaction surface 118 to drive the keel punch into the resected tibial surface. As the first member 114 has a length substantially the same or greater than the length of the keel punch 140, this provides an efficient transfer of impaction force along the entirety of the keel punch 140.

Figure 5:
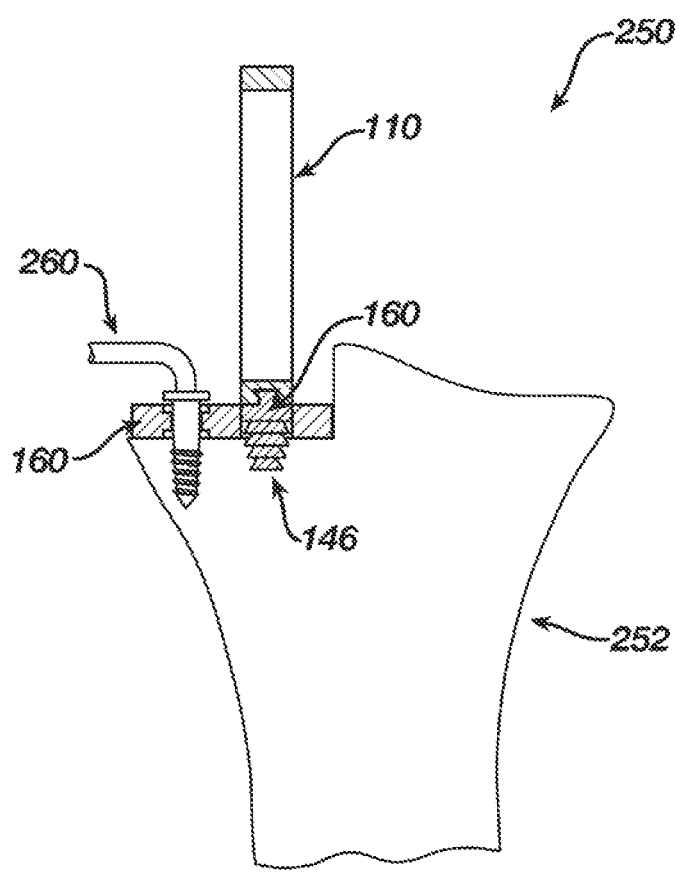
FIG. 5 shows an assembly of the kit of parts illustrated in FIGS. 1 to 3 during the method illustrated in FIG. 4.

With temporary reference to FIG. 5, there is shown an anterior view 250 of a tibia 252 of a patient at various stages during the method illustrated in FIG. 4. As illustrated in FIG. 5, if tibial 252 is a right hand tibia, then the procedure is being carried out on the lateral part of the tibia. Alternatively, if tibia 252 is a left hand tibia, then the procedure is being carried out on a medial part of a tibia. Irrespective, FIG. 5 shows a cross-sectional view through an assembly of the instrumentation on the resected tibia 252. As illustrated, the tibial trial 160 is mounted on the resected portion of the tibia and the keel punch 140 has been driven into the tibial bone using impactor 110 and the cutting formations 146 have formed a slot in the resected portion of the tibia.

Returning to FIG. 4, at 228, the impactor 110 is removed by sliding the impactor 110 in a generally anterior direction. It will be appreciated that previously, the handle used to initially place the tibial trial 160 will have been removed to facilitate ease of access and remove clutter from the surgical site. However, the keel punch 140 is left in place to improve the stability of the tibial trial 160 on the tibia. Also, removing the impactor 110 frees up space in the surgical site for further activities. At 230, the drill guide 174 is used to form a hole in the resected portion of the tibia for receiving a peg of the prosthetic tibial implant. As illustrated in FIG. 5, the universal joint drill 260 may be used to drill a hole in the tibia via drill guide 174. Alternatively, a flexible reamer may be used to form a hole in the tibia via guide 174. Once the peg hole has been formed in the tibia, then the drill or reamer is removed. Then, at 232, a suitably sized bearing trial component 190 is selected and a handle attached to facilitate handling and placement of the bearing trial component 190 on the tibial trial 160. In particular, the male dovetail formation 144 on the keel punch 140 is engaged with the dovetail slot 196 in the lower portion of the bearing trial component which is then urged generally in the posterior direction to slidingly attach to the tibial trial. Hence, the completed tibial trial has now been assembled in the joint space.

At 234, a femoral trial component is placed on the resected femur and impacted thereon. Then at 236, the trial joint may be reduced, and trialling of the knee joint carried out in a generally conventional way. Once trialling of the knee joint has been completed at 236, the remainder of the procedure may be carried out generally as conventionally. However, specific to the trialling kit of parts described herein, initially, the bearing trial component is removed by reattaching a handle and pulling the bearing trial component in a generally anterior direction. The impactor 110 is then used again to slidingly engage the keel punch 140 and remove that from the tibial trial. The bone pin is then removed and then the handle reattached to connect 184 to allow the tibial trial 160 to be removed. Hence, the tibia has now been prepared for receipt of the prosthetic tibial implant itself. If a cemented implant is used, then cement may be applied before implanting the prosthetic tibial component. Alternatively, in a cementless tibial component, then the tibial component may simply be located in the joint space and impacted. The tibial trialling instrumentation described above has already been used to form the slot for receiving the keel and a hole for receiving a peg of the prosthetic tibial implant.

FIG. 6 shows a further unicondylar tibial trial 300. FIG. 6 shows a view from an underside of the tibial trial 300. The tibial trial 300 has certain features in common with that described previously but has other features different thereto. As illustrated in FIG. 6, the tibial trial 300 has a body 302 in a generally plate like form with an underside 304, an anterior end 306 and a posterior end 308. FIG. 7 shows a view of a cross section along line A-A' of FIG. 6 of the tibial trial 300, further illustrating the upper surface 310 thereof. The tibial trial 300 includes an integral keel punch or broach 312 provided by a plurality of stepped sharp edges arranged in a generally pyramidal configuration. As best illustrated in FIG. 6, the keel punch 312 extends along an anterior-posterior axis of the tibial trial 300 and also, as illustrated in FIG. 7, extends in a generally inferior direction from the under surface 304.

A further punch or broach 320 is also provided extending in an inferior direction from the under surface 304 of the tibial trial 300. The further punch 320 is disposed to the side of the keel punch 312 and has a generally circular cylindrical shape of a plurality of concentric sharp cutting edges. The second punch 320 is configured and arranged to form a generally circular hole in the resected surface of the tibia in use, to accommodate a peg of a prosthetic tibial implant.

As best illustrated in FIG. 7, a male dovetail shaped formation 330 extends from the upper surface 310 of the tibial trial 300 and generally along the anterior-posterior axis of the tibial trial 300. The male dovetail formation 330 has a generally similar form and purpose as the dovetail formation 144 on the keel punch 140.

Hence, tibial trial 300 may be used in the kit of parts 100 in place of the tibial trial 160 and keel punch 140.

Optionally, the tibial trial 300 may include a lip or other formation extending in a generally inferior direction from the underside of an anterior part of the tibial trial 300. The anterior lip is arranged and configured to limit the position of the tibial trial 300 on a resected surface of the patient's tibia by engaging an anterior portion of the tibia control the position of the tibial trial relative to resected surface of the tibia in the anterior-posterior direction.

FIG. 6 shows a shape matched tibial trial 300 in which the shape of the body 302 substantially matches the typical shape of the resected portion of a typical tibia. FIG. 8 shows an alternative version 400 of the tibial trial shown in FIG. 6 having a non-shape matched body 402. Similarly, to tibial trial 300, tibial trial 400 also includes an integral keel punch 412 extending along an anterior-posterior axis and in an inferior direction from an underside 404 of the tibial trial 400. Similarly, a further punch or broach 420 is provided on the under surface 404 to a side of the keel punch 412 including a plurality of cutting formations configured and arranged to form a circular hole in a resected surface of the patient's tibia similar to further punch 320. Similarly, to tibial trial 300, tibial trial 400 may optionally include an anterior lip portion extending in an inferior direction from the underside 404 and arranged to limit the position of the tibial trial 400 on a resected surface of the tibia in the anterior-posterior direction. Owing to the similarity in construction, FIG. 7 also corresponds to a cross sectional view of tibial trial 400 along line B-B'.

Figure 9:
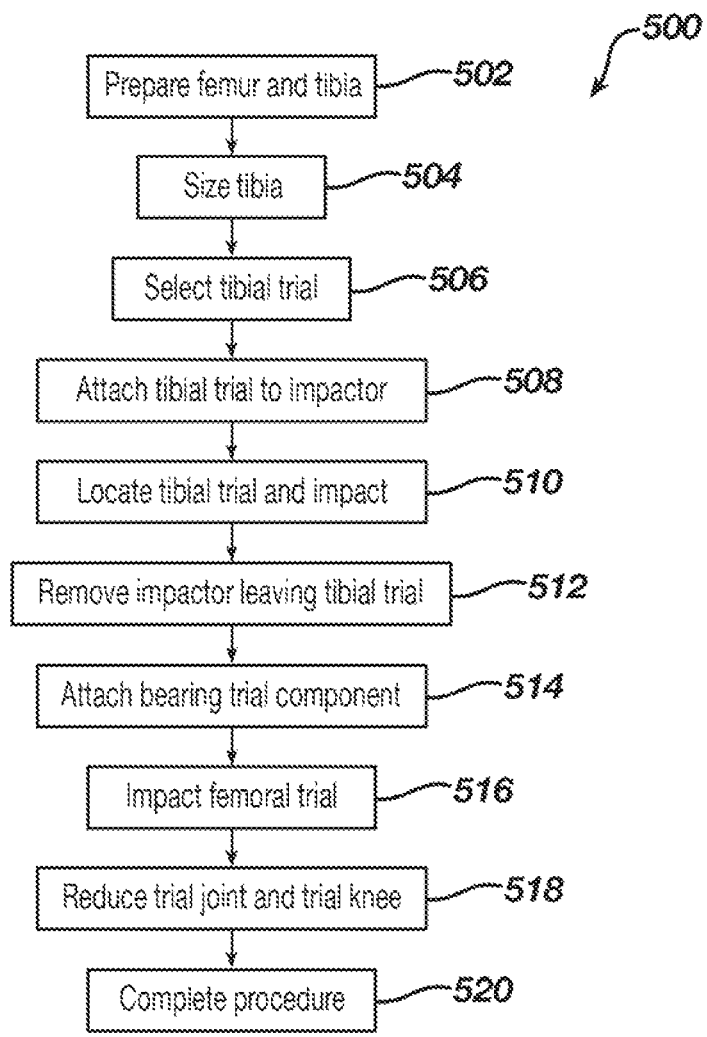
FIG. 9 shows a flow chart illustrating a further method according to a further aspect of the disclosure of using a kit of parts including the instruments illustrated in FIGS. 6 to 8.

A method of use of tibial trial 300 or 400 in a unicondylar knee replacement surgical procedure will now be described with reference to FIG. 9. FIG. 9 shows a flow chart illustrating a unicondylar knee replacement surgical procedure 500 which may be carried out using the tibial trial 300 of FIG. 6 or tibial trial 400, together with impactor 110 and bearing trial component 190.

FIG. 9 shows a flowchart illustrating a further method of carrying out a unicondylar knee replacement procedure on a patient and focussing in particular, on the trialling steps thereof. The method 500 illustrated in FIG. 9 has various steps similar to those of the method 210 illustrated in FIG. 4.

Similarly, the method begins at 502 by preparation of the femur and tibia and making of the femoral and tibial cuts.

At 504, the required size of the tibial implant can be determined similarly to 214 using tibial sizers. The kit of surgical instrumentation includes a plurality of tibial trials as illustrated in FIG. 6 or 8 each having a different size. Hence, at 506, a tibial trial of the appropriate size is selected from the plurality of tibial trials. Then, the impactor 110 is attached to the selected tibial trial by sliding the male dovetail formation 330 into the female dovetail channel 120 of the impactor 110. The impactor 110 is then used to position the tibial trial 300, 400 in the joint space and above the resected tibial surface at 510. An impaction tool, such as a mallet, may then be used to strike the strike surface 118 of the impactor 110 to drive the keel punch and hole punch formations of the tibial trial into the resected tibial surface at the same time. Once the tibial trial sits flush against the resected tibial surface, the impactor 110 may be removed by being withdrawn in the generally anterior direction, leaving the tibial trial 300, 400 seated on the resected tibial surface.

Then, similarly to 232, at 514, the bearing trial component is attached to the tibial trial to form the completed tibial trial. At 516, the femoral trial is impacted on the resected surfaces of the femur. Then at 518, the trial joint is reduced, and the knee is trialled. After trialling has been completed at 518, at 520, the bearing trial component is removed and then the impactor 110 reattached to the tibial trial 300, 400 so as to pool the hole punch and keel punch out of the resected tibial surface so as to remove the tibial trial from the joint space.

The remainder of the surgical procedure can then be completed at 520 generally described above and in a generally conventional manner.

The instrumentation described herein may be made from any suitable biologically safe material including metals, and alloys therefore, including stainless steel, aluminium or titanium alloys. However the bearing trial component will typically be made from a plastic and in particular polymers such as polyethylene, polyphenylsulfone (PPSU), polyether ether ketone (PEEK) or polyoxymethylene (POM).

Hence, the described instrumentation and surgical methods address a number of issues relating to tibial preparation during unicondylar knee replacement procedures. In particular, they help to address issues relating to reduced joint space access available during tibial preparation. Typically, the anterior cruciate ligament is still in place during a unicondylar knee replacement for surgical procedure. However, using the instrumentation of the present disclosure, there is no need to sub-lux the tibia in order to be able to drill peg holes for subsequently receiving a peg on the prosthetic tibial component.

Further, multiple different sizes of prosthetic components can be trialled using a reduced amount of surgical instrumentation owing to the modular nature of the instrumentation set.

Further, the impactor may facilitate reliable forming of the keel slot and may also serve multiple purposes in both handling and positioning various parts of the instrumentation set and also removing them from the surgical site.

Further, the tibial trials 300, 400 may reduce the number of steps required by permitting the keel slot and peg hole to be formed in a single impaction step rather than requiring multiple steps. Also, no further instrumentation needs to be introduced into the joint space in order to form the keel slot and peg hole.

Hence, it would be apparent that there are a number of different benefits provided by the various sets of instrumentation described herein and methods enabled thereby.

In this specification, example embodiments have been presented in terms of a selected set of details. However, a person of ordinary skill in the art would understand that many other example embodiments may be practiced which include a different selected set of these details. It is intended that the following claims cover all possible example embodiments.

The flowchart steps in the above Figures may be executed in other orders, unless a specific order is inherently required or explicitly stated. Also, those skilled in the art will recognize that while one example methods have been discussed, the material in this specification can be combined in a variety of ways to yield other examples as well, and are to be understood within a context provided by this detailed description.

While the disclosure is amenable to various modifications and alternative forms, specifics thereof have been shown by way of example in the drawings and described in detail. It should be understood, however, that other embodiments, beyond the particular embodiments described, are possible as well. All modifications, equivalents, and alternative embodiments falling within the scope of the appended claims are also envisaged.

The invention claimed is:

1. A kit of parts for use in a unicondylar knee replacement procedure, the kit of parts comprising:
    a keel punch having an inferior side and a superior side, the keel punch including a cutting formation on the inferior side and configured to form a slot in a resected part of a tibia of a patient in use and a first attachment formation on the superior side;
    a unicondylar tibial trial comprising a body having an upper surface, a lower surface, an anterior end and a posterior end, the body defining a slot passing through the body and between the upper surface and the lower surface and wherein the slot extends parallel to a longitudinal axis of the body extending from the anterior end to the posterior end and wherein the slot is configured to slidably receive the keel punch in use;
    a spike on an anterior part of the unicondylar tibial trial and extending in a posterior direction and arranged to engage an anterior portion of the tibia of the patient in use to secure the unicondylar tibial trial to the tibia of the patient; and
    an impactor, wherein the impactor includes a second attachment formation and the impactor is releasably attachable to the keel punch by slidingly engaging the second attachment formation of the impactor with the first attachment formation of the keel punch.

2. The kit of parts as claimed in claim 1 wherein the body further comprises a handle attachment formation adjacent the anterior end of the body for releasably receiving a handle.

3. The kit of parts as claimed in claim 1, wherein the body defines a plane and wherein the anterior part of the anterior end of the body defines a first aperture for receiving a pin for fixing the unicondylar tibial trial to the resected part of the tibia of the patient and wherein the first aperture extends along a first axis that is inclined relative to the plane of the body.

4. The kit of parts as claimed in claim 1, wherein the anterior part of the anterior end of the body also defines a second aperture for receiving a pin for fixing the unicondylar tibial trial to the resected part of the tibia of the patient and wherein the second aperture extends along a second axis that is inclined relative to the plane of the body.

5. The kit of parts as claimed in claim 4, wherein the first axis is configured to permit the pin to engage the tibia of the patient when the unicondylar tibial trial is seated in a first state on a medial resected part of the tibia and wherein the second axis is configured to permit the fixing to engage the tibia of the patient when the unicondylar tibial trial is seated in a second state on a lateral resected part of the tibia and wherein the unicondylar tibial trial is inverted in the second state compared to the first state.

6. The kit of parts as claimed in claim 1, wherein the body further defines a drill guide passing through the body between the upper surface and the lower surface and arrange to receive a drill to allow a peg hole to be drilled in the resected portion of the tibia of the patient.

7. The kit of parts as claimed in claim 6, wherein the drill guide defines a drill guide axis and wherein the drill guide axis is perpendicular to a plane defined by the lower surface of the body.

8. The kit of parts as claimed in claim 1, wherein the unicondylar tibial trial is mirror symmetric about a plane parallel to the upper surface and lower surface so that the unicondylar tibial trial can be inverted to be used on either a medial or a lateral resected part of the tibia.

9. The kit of parts as claimed in claim 1, and further comprising:
a further keel punch including a further cutting formation configured to form a slot in the resected part of the tibia of the patient in use, wherein the further keel punch is configured to be slidably received within the slot of the unicondylar tibial trial, wherein the cutting formation and the further cutting formation are different.

10. The kit of parts as claimed in claim 9, wherein the cutting formation has a different length and/or a different depth and/or a different width compared to the further cutting formation.

11. The kit of parts as claimed in claim 9 and further comprising:
a further unicondylar tibial trial, and wherein the further unicondylar tibial trial has a different size compared to the unicondylar tibial trial.

12. The kit of parts as claimed in claim 1, and further comprising:
a trial bearing, wherein the trial bearing includes a bearing attachment formation, and wherein the trial bearing is releasably attachable to the keel punch by mating the bearing attachment formation with the first attachment formation.

13. A kit of parts for use in a unicondylar knee replacement procedure, the kit of parts comprising:

a keel punch having an inferior side and a superior side, the keel punch including a cutting formation on the inferior side and configured to form a slot in a resected part of a tibia of a patient in use and a first attachment formation on the superior side;
a unicondylar tibial trial comprising a body having an upper surface, a lower surface, an anterior end and a posterior end, the body defining a slot passing through the body and between the upper surface and the lower surface and wherein the slot extends parallel to a longitudinal axis of the body extending from the anterior end to the posterior end and wherein the slot is configured to slidably receive the keel punch in use; and
an impactor, wherein the impactor includes a second attachment formation and the impactor is releasably attachable to the keel punch by slidingly engaging the second attachment formation of the impactor with the first attachment formation of the keel punch,
wherein the first attachment formation is a male formation and the second attachment formation is a female formation and wherein the male formation is slidingly receivable within the female formation.

14. The kit of parts as claimed in claim 13, wherein the unicondylar tibial trial is mirror symmetric about a plane parallel to the upper surface and lower surface so that the unicondylar tibial trial can be inverted to be used on either a medial or a lateral resected part of the tibia.

15. A kit of parts for use in a unicondylar knee replacement procedure, the kit of parts comprising:
a keel punch having an inferior side and a superior side, the keel punch including a cutting formation on the inferior side and configured to form a slot in a resected part of a tibia of a patient in use and a first attachment formation on the superior side;
a unicondylar tibial trial comprising a body having an upper surface, a lower surface, an anterior end and a posterior end, the body defining a slot passing through the body and between the upper surface and the lower surface and wherein the slot extends parallel to a longitudinal axis of the body extending from the anterior end to the posterior end and wherein the slot is configured to slidably receive the keel punch in use; and
an impactor, wherein the impactor includes a second attachment formation and the impactor is releasably attachable to the keel punch by slidingly engaging the second attachment formation of the impactor with the first attachment formation of the keel punch,
wherein the impactor comprises:
a first member bearing the second attachment formation;
a second member providing an impaction surface; and
an intermediate member extending between the first member and second member and spacing the second member apart from and above the first member.

16. The kit of parts as claimed in claim 15, wherein the impaction surface defines a first plane, the first member defines a second plane and the first plane and the second plane are parallel.

17. The kit of parts as claimed in claim 15, wherein the first member is as long as or is longer than the length of the keel punch.

18. The kit of parts as claimed in claim 15, wherein the unicondylar tibial trial is mirror symmetric about a plane parallel to the upper surface and lower surface so that the unicondylar tibial trial can be inverted to be used on either a medial or a lateral resected part of the tibia.

19. A kit of parts for use in a unicondylar knee replacement procedure, the kit of parts comprising:
- a keel punch having an inferior side and a superior side, the keel punch including a cutting formation on the inferior side and configured to form a slot in a resected part of a tibia of a patient in use and a first attachment formation on the superior side;
- a unicondylar tibial trial comprising a body having an upper surface, a lower surface, an anterior end and a posterior end, the body defining a slot passing through the body and between the upper surface and the lower surface and wherein the slot extends parallel to a longitudinal axis of the body extending from the anterior end to the posterior end and wherein the slot is configured to slidably receive the keel punch in use; and
- an impactor, wherein the impactor includes a second attachment formation and the impactor is releasably attachable to the keel punch by slidingly engaging the second attachment formation of the impactor with the first attachment formation of the keel punch, wherein the impactor generally has the form of a C-arm.

20. The kit of parts as claimed in claim 19, wherein the unicondylar tibial trial is mirror symmetric about a plane parallel to the upper surface and lower surface so that the unicondylar tibial trial can be inverted to be used on either a medial or a lateral resected part of the tibia.

\* \* \* \* \*